United States Patent [19]

Endo et al.

[11] 4,163,023

[45] Jul. 31, 1979

[54] TREATMENT OF PHOTOGRAPHIC PROCESSING SOLUTIONS

[75] Inventors: Akira Endo; Tohru Kitahara, both of Odawara, Japan

[73] Assignee: Fuji Photo Film Co., Ltd., Kanagawa, Japan

[21] Appl. No.: 746,753

[22] Filed: Dec. 2, 1976

[30] Foreign Application Priority Data

Dec. 2, 1975 [JP] Japan ................................ 50-143537
Oct. 19, 1976 [JP] Japan ................................ 51-125838

[51] Int. Cl.$^2$ .................... C07C 143/75; C07C 91/06; C07C 87/58; G03C 5/30; G03C 7/30

[52] U.S. Cl. .................................... 260/556 A; 96/55; 96/66.3; 210/40; 252/426; 260/501.17; 260/501.2; 260/573; 260/575; 260/578; 260/708; 260/343.7; 260/583 DD; 544/170; 548/356; 548/363

[58] Field of Search ........... 260/575, 578, 708, 556 A, 260/573, 501.17, 501.2; 252/426; 96/55, 66.3; 210/40

[56] References Cited

U.S. PATENT DOCUMENTS 2,358,053 9/1944 Brunings .............................. 260/574
3,253,920 5/1966 Rees et al. ............................... 96/55
3,936,394 2/1976 Kusunose et al. ............... 252/426 X

FOREIGN PATENT DOCUMENTS 478885 11/1951 Canada .................................... 260/575

OTHER PUBLICATIONS

Volynkin et al., CA 81: 140603W, (1974).
Walser, CA 70: 99441z, (1969).
Seidl et al., CA 84: 50239q, (1976).
Vinson et al., CA 79: 128981u, (1973).
Wolf et al., CA 64: 8330c, (1966).

*Primary Examiner*—Thomas Waltz
*Attorney, Agent, or Firm*—Sughrue, Rothwell, Mion, Zinn and Macpeak

[57] ABSTRACT

A process of selectively separating a developing agent and/or a color development accelerator such as benzyl alcohol, etc., from photographic processing solutions containing these materials by bringing the processing solutions into contact with a copolymer selected from the group consisting of a styrenedivinylbenzene copolymer and a methacrylic acid monoestermethacrylic acid polyester copolymer. The developing agent thus adsorbed on the copolymer can be recovered therefrom by treating the copolymer with, e.g., diluted sulfuric acid.

9 Claims, No Drawings

TREATMENT OF PHOTOGRAPHIC PROCESSING SOLUTIONS

BACKGROUND OF THE INVENTION

1. Field of the Invention

This invention relates to a process of separating a developing agent and/or a color development accelerator such as benzyl alcohol, etc., from a photographic processing solution and, more particularly, it relates to a process of selectively separating the aforesaid specific processing component or components from a photographic processing solution containing one or both of these materials by bringing the processing solution into contact with a copolymer selected from the group consisting of a styrene-divinylbenzene copolymer and a methacrylic acid monoester-methacrylic acid polyester copolymer.

2. Description of the Prior Art

In the formation of photographic images using silver halide photographic materials, various processing solutions such as developer solutions, stop solutions, fix solutions, bleach solutions (or blix solutions in place of fix solutions and bleach solutions), hardening solutions, neutralization solutions, alkali pre-treatment bath solutions, stabilization solutions, etc., are used.

One particular photographic processing solution contains a developing agent and other various compounds and sometimes after dissolving a part or all of these processing components in water for preparing the photographic processing solution, a specific component or specific components must be removed or separated from the processing solution. Examples of photographic processing solutions from which a specific processing component or components must be removed or recovered are spent photographic processing solutions, a part or all of the photographic processing solutions which became useless after their preparation, or photographic processing solutions which partially overflow from developer baths at the time of supplying the processing solutions thereto as development progresses.

Moreover, since photographic processing solutions generally contain organic compounds having a high biological oxygen demand (hereinafter, referred to as BOD) or a high chemical oxygen demand (hereinafter, referred to as COD), the direct discharge of these photographic processing solutions into sewers or rivers greatly tends to cause environmental pollution or contamination.

Accordingly, in discharging such photographic processing solutions, the materials which tend to cause environmental pollution must be removed, the photographic processing solutions must be rendered harmless, remaining effective processing components must be recovered from the photographic processing solutions, or two or more such treatments in combination must be applied to the processing solutions before discharging. Developing agents and color development accelerators such as benzyl alcohol, etc., contained in photographic developers have a particularly high BOD and COD and, hence, if these components are previously removed or separated from a developer solution when such is to be discharged, the developer solution can be easily treated for waste disposal. Furthermore, since the developing agents, etc., contained in developer solutions are generally expensive, it is undesirable to simply decompose these components in waste treatment and it is desirable from an economical viewpoint to recover these processing components in some manner for reuse.

Various processes have hitherto been proposed for separating or recovering specific components from photographic processing solutions. For instance, a process in which a developing agent, benzyl alcohol, etc., is recovered from a developer solution by adding thereto a salt such as sodium sulfate, etc., to cause salting-out as described in the specification of Japanese Patent Publication No. 33698/73; a process in which these components are extracted using an organic solvent as described in the specification of U.S. Patent No. 2,358,053; and a process in which a dissociated developing agent, etc., is recovered using an ion-exchange resin as described in the specification of U.S. Pat. No. 3,253,920, have been proposed. Furthermore, a proces has also been proposed in which these specific processing components are separated or removed from photographic processing solutions by bringing the processing solutions into contact with activated carbon.

However, these conventional processes as described above are all insufficient from an economical viewpoint. That is, in the above-described salting-out process, a large amount of salt is required to perform the process, which results in increasing the operational cost and further since sparingly soluble compounds are all deposited in the proposed process, complicated steps are required or recovery of each component in a pure form from the solution of a mixture of the salts of these components is difficult. Furthermore, since it is not easy to adjust the pH of the processing solution prior to the addition of a salt for performing the salting-out process, it is very difficult or unsuitable to employ such a salting-out process in laboratories having poor facilities or equipment. In the organic solvent extraction process, a large amount of solvent is used, which increases the operational cost for the process, and further an additional means is required for preventing the occurrence of fire and for maintaining safety and hygiene, which results in increasing the installation cost. Furthermore, since the organic solvent for extraction is dissolved in a photographic processing solution during the operation of the process, it becomes difficult to maintain the values of BOD and COD in the processing solution at a definite level. The ion-exchange resin process as proposed above is very low in efficiency when the compounds to be recovered are not in dissociated states. Consequently, it is very difficult to remove or recover color developing agents such as p-phenylenediamines and 3-pyrazolones using such an ion-exchange resin process. Also, it is impossible to recover color development accelerators such as benzyl alcohol, etc., which are nondissociatable compounds, with the ion-exchange resin process. The adsorption removal process with activated carbon may be excellent in workability and separation efficiency of organic compounds from an aqueous processing solution but almost all organic materials are strongly adsorbed on activated carbon employed at the practice of this process. Thus, complicated and high cost techniques are involved to recover the adsorbed materials by elution. Also, it is difficult or troublesome to regenerate the activated carbon once used and, in addition, the cost required for regenerating the activated carbon is high. Furthermore, it is also difficult to dispose of the activated carbon once used. Moreover, activated carbon is subdivided into powders at use due to its comparatively low mechanical strength and thus it is scattered off or enters into the processing solution as a powder. Therefore, in using activated carbon, a complicated procedure is required for preventing the occurrence of the above-described difficulties.

SUMMARY OF THE INVENTION

An object of this invention is, therefore, to provide a novel process of selectively separating comparatively expensive developing agents and/or color development accelerators from photographic processing solutions.

Another object of this invention is to provide a process of removing developing agents and/or color development accelerators from photographic processing solutions by a comparatively simple and easy operation.

Still another object of this invention is to provide a process for removing developing agents and/or color development accelerators such as benzyl alcohol, etc., from spent photographic processing solutions for discharging safely these solutions without causing pollution into sewers or rivers due to the above materials having a high BOD and COD.

As the result of various investigations, it has now been discovered that the above-described objects of this invention can be attained by bringing a photographic processing solution containing the aforesaid component or components into contact with a copolymer selected from the group consisting of a styrene-divinylbenzene copolymer and a methacrylic acid monoester-methacrylic acid polyester copolymer. That is, according to this invention, there is provided a process of separating a developing agent and/or a color development accelerator from a photographic processing solution which comprises bringing the photographic processing solution into contact with a styrene-divinylbenzene copolymer or a methacrylic acid monoester-methacrylic acid polyester copolymer (hereinafter, referred to as methacrylate copolymer).

DETAILED DESCRIPTION OF THE INVENTION

In the styrene-divinylbenzene copolymer described above, a suitable weight ratio of the styrene to the divinylbenzene can range from about 99:1 to about 1:1.

In describing the methacrylate copolymer used in this invention, the term "methacrylic acid monoester" means a monoester of methacrylic acid and a monohydric alcohol or polyhydric alcohol, and the term "methacrylic acid polyester" means a polyester of methacrylic acid and a polyhydric alcohol. Suitable examples of monohydric alcohols include methanol, ethanol, isopropanol, propanol, butanol, pentanol, hexanol, octanol, 2-ethylhexanol, dodecyl alcohol, etc., and suitable examples of polyhydric alcohols include ethylene glycol, 1,3-propylene glycol, 1,2-propylene glycol, butylene glycol, glycerin, trimethylolpropane, trimethylolethane, pentaerythritol, polyethylene glycol, etc.

Suitable examples of methacrylic acid monoesters include methyl methacrylate, ethyl methacrylate, propyl methacrylate, butyl methacrylate, 2-hydroxyethyl methacrylate, 2-hydroxypropyl methacrylate, etc. Examples of methacrylic acid polyesters are ethylene glycol dimethacrylate, polyethylene glycol dimethacrylates having a polyethylene glycol polymerization degree of 2 to 10 such as diethylene glycol dimethacrylate and triethylene glycol dimethacrylate, trimethylolpropane trimethacrylate and pentaerythritol tetramethacrylate. Among the above compounds, ethylene glycol dimethacrylate is most preferred, and polyethylene glycol ($n=2$ to 10)dimethacrylate is also preferred.

A suitable amount of the methacrylic acid monoester in the methacrylate copolymer can range from about 5 to about 95% by weight and a suitable amount of the methacrylic acid polyester therein can range from about 95 to about 5% by weight. A preferred amount of the methacrylic acid polyester in the methacrylate copolymer is less than about 50% by weight, and particularly is from 20 to 5% by weight.

The methacrylic acid polyester can act as a cross linking agent.

The methacrylate copolymer can further contain an ethylenically unsaturated monomer such as an acrylate (e.g., methyl acrylate, ethyl acrylate, propyl acrylate, butyl acrylate, 2-hydroxylethyl acrylate, hexylacrylate, etc.), acrylonitrile, vinyl acetate, styrene or acrylamide. A suitable amount of the ethylenically unsaturated monomer which can be present in the methacrylate copolymer can range from about 1 to about 50% by weight, preferably 5 to 30% by weight.

In using the styrene-divinylbenzene copolymer and the methacrylate copolymer in this invention, the elution of the adsorbed materials from the both copolymers is far easier than in using activated carbon and thus the copolymers once used can be easily regenerated for repeated reuse without degrading the function of the copolymers by treating the copolymers with an appropriate solvent. This makes the process of this invention quite advantageous from an economic standpoint and easy in handling and operation.

It is to be understood that the styrene-divinylbenzene copolymer and the methacrylate copolymer of this invention can be used individually or as a mixture thereof. Where mixtures are employed, a preferred weight ratio of the styrene-divinylbenzene copolymer to the methacrylate copolymer is about 1:1.

The styrene-divinylbenzene copolymer and the methacrylate copolymer (these two copolymers will be referred to hereinafter simply as the "copolymer") used in this invention may have any structure but it is preferred that the copolymer be porous and have a large specific surface area. Practically, copolymers having a pore volume of about 0.1 to about 3 ml/g and a specific surface area of about 1 to about 2,000 $m^2/g$ are preferably used in this invention.

The porous copolymer used in this invention can be prepared using any process. In general, however, a porous copolymer or polymer is prepared by (1) a process in which the polymerization is carried out in the presence of a diluent which does not take part in the polymerization, (2) a process in which the polymerization is carried out in the presence of a polymer which does not take part in the polymerization, or (3) a process in which the polymerization is carried out in the presence of both a polymer and a diluent as described above, neither of which takes part in the polymerization.

In the polymerization process using a diluent which does not take part in the polymerization, a polymer or copolymer having a porous structure is formed by conducting the polymerization after adding to the polymerization system a diluent which does not take part in the polymerization and is a good solvent for the monomer or monomers used but is a nonsolvent which does not swell the polymer or copolymer formed or swells such only to a small extent. Examples of diluents which can be used for the purpose are alcohols such as t-amyl alcohol, sec-butyl alcohol, etc.; aliphatic hydrocarbons such as hexane, iso-octane, etc.; and aromatic hydrocarbons such as toluene, ethylbenzene, diethylbenzene, etc., and the amount of the diluent employed generally is about 20 to 50% by volume to the volume of the polymerization system. When the copolymerization of styrene and divinylbenzene or the formation of the methacrylate copolymer is carried out by this process, the above-described diluent can be appropriately employed regardless of the ratio of starting materials used, the reaction temperature employed, and the reaction period of time utilized.

In the polymerization process using a polymer which does not take part in the polymerization, a porous polymer or copolymer is obtained by adding to the polymerization system a linear copolymer or polymer such as a copolymer of ethyl maleate and vinyl acetate, a copolymer of ethyl maleate and methyl methacrylate, a copolymer of ethyl maleate and acrylonitrile, a polyethylene glycol having a molecular weight of about 5,000 to about 50,000, and polystyrene having a molecular weight of about 50,000 to about 100,000 as a filler followed by polymerization and dissolving out the linear polymer or copolymer after the polymerization is over.

Also, in the polymerization process using the polymer and the diluent which do not take part in the polymerization, a polymer or copolymer having a porous structure is obtained in the same manner as described in the case of performing the polymerization in the presence of the polymer which does not take part in the polymerization using an aromatic hydrocarbon such as dichloroethane, xylene, toluene, etc., together with the above-described linear polymer or copolymer.

The polymerization or copolymerization processes as described above can be used for preparing the porous copolymers of styrene and divinylbenzene and the porous methacrylate copolymers used in this invention. Among these copolymers prepared by these processes as described above, copolymers having a specific surface area of about 100 to about 700 $m^2/g$, a pore volume of about 0.2 to about 1.5 ml/g, and a pore radius of about 30 to about 2,000 Å are particularly preferred in this invention since such copolymers have a high adsorptivity and the adsorbed materials are readily removed therefrom by elution. Specific examples of commercially available styrene-divinylbenzene copolymers having the above-indicated preferred properties are High Porous Polymer made by Mitsubishi Chemical Industries Co., Ltd. and Amberlite XAD-2, Amberlite XAD-4, etc., produced by Rohm & Haas Co., and examples of commercially available methacrylate copolymers having these properties are Amberlite XAD-7, Amberlite XAD-8 and Amberlite XAD-9, all produced by Rohm & Haas Co.

The developing agents which can be separated from photographic processing solutions containing these materials by the process of this invention include polyhydroxybenzenes (e.g., hydroquinone, chlorohydroquinone, bromohydroquinone, isopropylhydroquinone, toluhydroquinone, methylhydroquinone, 2,3-dichlorohydroquinone, 2,5-dimethylhydroquinone, pyrogallol, catechol, etc.), 3-pyrazolidones (e.g., 1-phenyl-3-pyrazolidone, 1-phenyl-4-methyl-3-pyrazolidone, 1-phenyl-4,4-dimethyl-3-pyrazolidone, 1-phenyl-4-ethyl-3-pyrazolidone, 1-phenyl-5-methyl-3-pyrazolidone, etc.), aminophenols (e.g., o-aminophenol, p-aminophenol, N-methyl-o-aminophenol, N-methyl-p-aminophenol, 4-N-benzylaminophenol, 2,4-diaminophenol, etc.), ascorbic acid, 1-aryl-3-aminopyrazolines (e.g., 1-(p-hydroxyphenyl)-3-aminopyrazoline, 1-(p-methylaminophenyl)-3-pyrazoline, 1-(p-aminophenyl)-3-aminopyrazoline, 1-6-amino-m-methylphenyl)-3-aminopyrazoline, etc.), hydroxylamines (e.g., hydroxylamine, N,N-diethylhydroxylamine, N-hydroxylmorpholine, and also the compounds described in the specifications of British Pat. Nos. 1,327,032, 1,327,033, 1,327,034 and 1,327,035, etc.), p-phenylenediamines (e.g., N,N-diethyl-p-phenylenediamine, N,N-diethyl-3-methyl-p-phenylenediamine, 4-amino-3-methyl-N-ethyl-N-methanesulfoamidoethylaniline, 4-amino-3-methyl-N-ethyl-N-hydroxyethylaniline, N-ethyl-N-hydroxyethyl-p-phenylenediamine, and also the compounds described in the specifications of U.S. Pat. Nos. 2,193,015 and 2,592,364 and Japanese Patent Application (OPI) No. 64933/73, etc.), and the salts (e.g., hydrochlorides, sulfates, nitrates, p-toluene-sulfonates, etc.) of these compounds.

Also, the color development accelerators which can be separated from photographic processing solutions containing these materials by the process of this invention are the compounds acting as development accelerators at color development and they include the compounds represented by the following general formula (I):

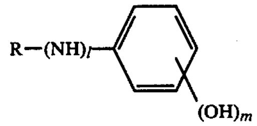

(I)

wherein R represents a hydrogen atom, a methyl group, an ethyl group, a methyl group substituted with a hydroxy group or an amino group, or an ethyl group substituted with a hydroxy group or an amino group; l is 0 or 1; and m is 0, 1 or 2; and straight chain or branched chain aliphatic alcohols having 4 to 6 carbon atoms.

Specific examples of color development accelerators are benzyl alcohol, α-phenylethyl alcohol, β-phenylethyl alcohol, aniline, N-phenylethanolamine, hydroxyphenylethyl alcohol, isobutyl alcohol, hexyl alcohol, etc.

The process of this invention can be practiced in various ways. For instance, the process of this invention can be practiced by placing the styrene-divinylbenzene copolymer or the methacrylate copolymer in a photographic processing bath or by collecting a photographic processing solution which has overflowed from a processing bath and placing the copolymer in the solution thus collected. In this case, the treatment by the copolymer may be performed in a batch-wise manner or a continuous manner.

Suitable techniques for bringing a photographic processing solution to be treated into contact with the copolymer include the use of the so-called column process in which the copolymer is packed in a layer form in, for instance, a cylindrical container and the processing solution is passed therethrough downwardly or upwardly. In some cases, the process of this invention can be performed by adding the copolymer to a photographic processing solution followed by stirring, allowing the copolymer to settle, and then recovering the copolymer by filtration. Furthermore, the process of this invention can be practiced by packing the copolymer in a container made of a filter material through which the photographic processing solution can be freely passed, placing the container containing the copolymer in the processing solution, and stirring the solution to adsorb the specific processing component or components on the copolymer. In the above-described processes, it is desirable for the contacting time to be as slow as possible. For example, with a batch operation where the copolymer is simply added to a photographic processing solution followed by stirring, a suitable contacting time is at least about 30 minutes and where a continuous operation is employed in which a photographic processing solution is passed through, for example, a column containing the copolymer packed therein, a suitable space velocity is less than about 15 l/hr. Further, it is desirable to conduct the contacting operation at a low temperature, for example, preferably not more than about 25° C. Of the above-described processes, the column process is most preferred since the apparatus and operation required are simple and the processing solution can be treated continuously.

The process of this invention can be applied to the treatment of any photographic processing solutions containing developing agents and/or color development accelerators used for processing various kinds of silver halide photographic materials such as, for example, black-and-white photographic materials, color negative photographic materials, color positive photographic materials, color reversal photographic materials, auto-positive type photographic materials, lithographic type photographic materials, auto-radiographic materials, etc. In addition, the process of this invention can be applied to the treatment of a photographic processing solution containing a developing agent and a color development accelerator and further can be, as a matter of course, applied to the treatment of a photographic processing solution containing either one or both of the two components.

Furthermore, the developing agent and/or the color development accelerator contained in a developer solution sometimes is carried over into subsequent processing baths or washing water and thus the process of this invention can be applied not only to developer solutions but also other processing solutions containing at least one of the above-described processing components.

Also, the process of this invention can be applied in treating processing solutions used for any type of development such as an automatic development using, for example, a hanger type automatic developing machine, a roller-conveyor type automatic developing machine, a belt conveying type automatic developing machine, etc., and a manual development such as a dish development, a tank development, etc.

According to the process of this invention, developing agents and/or color development accelerators can be effectively removed from photographic processing solutions in a simple manner, and the developing agents thus adsorbed by the copolymer can be separated therefrom at high concentration by treating the copolymer with an acid, etc.

More specifically, the copolymers once used can be easily regenerated by treating with acids, and the adsorbed developing agents and/or development accelerators are removed in the form of salt of the acid employed. Suitable examples of acids which can be used include sulfuric acid, hydrochloric acid, nitric acid, nitrous acid and the like. Of these, sulfuric acid is particularly preferred for regeneration of both copolymers and for recovery of the adsorbed material therefrom. The adsorbed materials can also be removed with an organic solvent (e.g., methylene chloride, ethyl acetate, chloroform, acetone, etc.), although the use of the organic solvent has some disadvantages, e.g., cost and also pollution problems.

In the recovery of the developing agent and/or color development accelerator removed from photographic processing solutions in accordance with this invention, use of sulfuric acid is inexpensive and when sulfuric acid is used, the treatment of the copolymer is easy. A suitable concentration for the sulfuric acid can range from about 2 to about 15% by weight, preferably 5 to 10% by weight. In separating the developing agent and/or color development acccelerator adsorbed on the copolymer using sulfuric acid, the resultant aqueous solution thereof can be then condensed to form salts. As a result, use of sulfuric acid at a concentration lower than about 2% by weight is not preferred since a long period of time is required to condense the solution and form salts. Where the concentration of the sulfuric acid is above about 15% by weight the yield of the salts obtained decreases. As a result, operation within the above-described range is desirable. A suitable temperature for separation of the developing agent and/or development accelerator from solution is a temperature of about 60° C. or higher.

The following Examples are given to illustrate the present invention in greater detail but the invention should not be construed as being limited to these Examples in any way. Unless otherwise indicated herein, all parts, percents, ratios and the like are by weight.

EXAMPLE 1

A developer having the following composition was prepared.

| | |
|---|---|
| 1-Phenyl-3-pyrazolidone-N-methyl-p-aminophenol Sulfate | 0.2 g |
| Sodium Sulfite | 50.0 g |
| Hydroquinone | 5.0 g |
| Sodium Carbonate | 10.0 g |
| Boric Acid | 5.0 g |
| Potassium Bromide | 1.0 g |
| Water to make | 1,000 ml |

Then, 250 ml of a styrene-divinylbenzene copolymer (particles having a mean diameter of about 1 mm, a specific surface area of 700 $m^2/g$, a pore volume of 1 ml/g and a mean pore diameter of 200 Å) was packed in an inside tube, having an inside diameter of 2 cm, of a double wall glass tube. Thereafter, 1 l of the developer thus prepared was passed through the column of the copolymer at room temperature (about 20°-30° C.) over a one hour period and then while passing water at 60° C. through the outer tube of the double walled tube, 200 ml of 1 N sulfuric acid heated to 60° C. was passed through the column of the copolymer over a period of 45 minutes. In this case, the passing rate of each solution was adjusted using a needle valve positioned at the outlet of the tube.

After treatment, the concentration of the developing agent in each solution was analyzed. The results obtained are shown in Table 1 below.

TABLE 1

| Processing Solution | 1-Phenyl-3-pyrazolidone (g/l) | N-Methyl-p-aminophenol (g/l) | Hydroquinone (g/l) |
|---|---|---|---|
| Developer before passing column | 0.19 | 2.91 | 4.86 |
| Developer after passing column | 0.00 | 0.19 | 2.25 |
| Sulfuric acid solution passed through the used copolymer | 0.05 | 13.05 | 11.8 |

The concentrations of sodium sulfite, sodium carbonate, boric acid, and potassium bromide in the developer were unchanged when the developer was passed through the column of the copolymer.

From these results as shown above, it can be understood that the developing agent contained in a developer can be effectively removed from the developer by bringing the developer into contact with a styrene-divinylbenzene copolymer and that the developing agent thus adsorbed on the copolymer can be recovered therefrom by bringing the copolymer into contact with 1 N sulfuric acid.

EXAMPLE 2

A color developer (40 l) having the following composition was prepared.

| | |
|---|---|
| Benzyl Alcohol | 12.0 g |
| Diethylene Glycol | 3.5 g |
| Sodium Hydroxide | 4.0 g |
| Sodium Sulfite | 2.0 g |
| Sodium Acetate | 10.0 g |
| Citric Acid | 3.0 g |
| Tartaric Acid | 3.5 g |
| Potassium Bromide | 0.4 g |
| Sodium Chloride | 1.0 g |
| Ethylenediamine Tetraacetic Acid Di-sodium Salt | 4.0 g |
| Hydroxylamine Sulfate | 2.0 g |
| 4-Amino-3-methyl-N-ethyl-N-(β-methanesulfonamidoethyl)aniline Sesquisulfate Monohydrate | 5.0 g |
| Water to make | 1,000 ml |

Using the color developer thus prepared, 100 $m^2$ of a color paper was processed.

Thereafter, 1 l each of the developer thus used was treated in one of the following three processings (A), (B) and (C).

(A) The spent developer was brought into contact with 100 ml of the styrene-divinylbenzene copolymer as used in Example 1 using the same double walled tube and in the same manner as in Example 1 and then the color developing agent was recovered using 1 N sulfuric acid.

(B) The same procedure as in (A) was followed using a column packed with 100 ml of activated carbon (Shirasagi, a trade name, made by Takeda Chemical Industries Co., Ltd., average particle size (diameter): about 0.4 mm) in place of the styrene-divinylbenzene copolymer.

(C) The same procedure as in process (A) was followed using a column packed with 100 ml of a strongly basic anion exchange resin, Amberlite IRA-400 (trade name, produced by Rohm & Haas Co.), in place of the styrene-divinylbenzene copolymer.

The composition of the solution passed through the column was analyzed in each case. The results obtained are shown in Table 2 below.

TABLE 2

| | Before Passing Column (g/l) | After Passing Column (A) (g/l) | (B) (g/l) | (C) (g/l) |
|---|---|---|---|---|
| Benzyl Alcohol | 12.1 | 2.0 | 1.1 | 12.0 |
| Diethylene Glycol | 3.4 | 3.3 | 1.5 | 3.4 |
| Sodium Acetate | 9.8 | 9.8 | 0.8 | 0.7 |
| Ethylenediamine Tetraacetic Acid Di-sodium Salt | 3.9 | 3.9 | 1.5 | 0.3 |
| Citric Acid | 2.9 | 2.9 | 0.0 | 0.2 |
| Tartaric Acid | 3.3 | 3.2 | 0.1 | 0.5 |
| 4-Amino-3-methyl-N-ethyl-N-(β-methanesulfonamidoethyl)-aniline Sesquisulfate Monohydrate | 4.9 | 0.5 | 0.6 | 4.8 |

As is clear from the above results, in process (A) wherein the color developer was brought into contact with the styrene-divinylbenzene copolymer, benzyl alcohol and the color developing agent, 4-amino-3-methyl-N-ethyl-N-(β-methanesulfonamidoethyl)aniline sesquisulfate monohydrate only were selectively removed from the developer.

On the other hand, in process (B) wherein the color developer was brought into contact with activated carbon, not only were the benzyl alcohol and the color developing agent separated but also the diethylene glycol, sodium acetate, ethylenediamine tetraacetic acid di-sodium salt, citric acid, and tartaric acid were removed from the developer. That is, it was impossible to only remove selectively the benzyl alcohol and the color developing agent using the activated carbon.

Furthermore, in process (C) wherein the color developer was brought into contact with the ion exchange resin, the color developing agent and benzyl alcohol were hardly removed from the developer.

EXAMPLE 3

In this example, the styrene-divinylbenzene copolymer used in Example 2 was regenerated and used repeatedly for the same purpose.

After passing water at 60° C. through the outer space of the double walled tube containing in the inside tube the styrene-divinylbenzene copolymer used in Example 2, 500 ml of 0.5 N sulfuric acid heated to 60° C. was passed through the column of the styrene-divinylbenzene copolymer over a period of 30 minutes. Thereafter, 4 l of city water was passed through the column of the copolymer over a period of 40 minutes to regenerate the styrene-divinylbenzene copolymer.

A spent color developer as in Example 2 was then brought into contact with the styrene-divinylbenzene copolymer thus regenerated and thereafter the copolymer was regenerated again using 0.5 N sulfuric acid. This procedure was repeated 30 times.

The compositions of the developer thus passed through the column of the copolymer at the 15th cycle and the 30th cycle are shown in Table 3 below.

TABLE 3

| | 15th Cycle (g/l) | 30th Cycle (g/l) |
|---|---|---|
| Benzyl Alcohol | 2.1 | 2.2 |
| Diethylene Glycol | 3.3 | 3.3 |
| Sodium Acetate | 9.8 | 9.8 |
| Ethylenediamine Tetraacetic Acid | | |

TABLE 3-continued

| | 15th Cycle (g/l) | 30th Cycle (g/l) |
|---|---|---|
| Di-sodium Salt | 3.9 | 3.9 |
| Citric Acid | 2.9 | 2.9 |
| Tartaric Acid | 3.2 | 3.2 |
| 4-Amino-3-methyl-N-ethyl-N-(β-methanesuflonamidoethyl)aniline Sesquisulfate Monohydrate | 0.5 | 0.6 |

The results show that the compositions of the color developer at the 15th cycle and the 30th cycle were substantially the same as that of the developer at the 1st cycle, that is, the composition of the developer passed through the column of the copolymer in process (A) of Example 2. Thus, it was confirmed that the styrene-divinylbenzene copolymer used in the experiment could be regenerated by the very simple operation of bringing the copolymer used into contact with sulfuric acid and water and the copolymer thus regenerated could be used 30 times without substantially reducing the function of the copolymer by repeating the same regeneration cycle.

EXAMPLE 4

A developer having the following composition was prepared.

| | |
|---|---|
| 1-Phenyl-3-pyrazolidone-N-methyl-p-aminophenol Sulfate | 0.2 g |
| Sodium Sulfite | 50.0 g |
| Hydroquinone | 5.0 g |
| Sodium Carbonate | 10.0 g |
| Boric Acid | 5.0 g |
| Potassium Bromide | 1.0 g |
| Water to make | 1,000 ml |

Then, 250 ml of a methyl methacrylate-ethylene glycol dimethacrylate copolymer (90:10 weight ratio, particles having a mean diameter of about 1 mm, a specific surface area of 300 $m^2/g$, a pore volume of 0.9 ml/g and a mean pore diameter of 150 A) was packed in the inside tube having an inside diameter of 2 cm of a double walled tube of glass. Thereafter, 1 l of the developer thus prepared was passed through the column of the copolymer at room temperature over a one hour period and then while passing water at 60° C. through the outer space of the double walled tube, 200 ml of 1 N sulfuric acid heated to 60° C. was passed through the column of the copolymer over a period of 45 minutes. In this case, the passing rate of each solution was adjusted using a needle valve positioned at the outlet of the tube.

After treatment, the concentration of the developing agent in each solution was analyzed. The results obtained are shown in Table 4 below.

TABLE 4

| Processing Solution | 1-Phenyl-3-pyrazolidone (g/l) | N-Methyl-p-aminophenol (g/l) | Hydroquinone (g/l) |
|---|---|---|---|
| Developer before passing column | 0.19 | 2.91 | 4.86 |
| Developer after passing column | 0.00 | 0.30 | 2.22 |
| Sulfuric acid solution passed through the used copolymer | 0.04 | 12.41 | 12.0 |

The concentrations of sodium sulfite, sodium carbonate, boric acid, and potassium bromide in the developer were unchanged when the developer was passed through the column of the copolymer.

From the results as shown above, it can be understood that a developing agent contained in a developer can be effectively removed from the developer by bringing the developer into contact with a methyl methacrylate-ethylene glycol dimethacrylate copolymer and that the developing agent thus adsorbed on the copolymer can be recovered therefrom by bringing the copolymer into contact with 1 N sulfuric acid.

EXAMPLE 5

A color developer (40 l) having the following composition was prepared.

| | |
|---|---|
| Benzyl Alcohol | 12.0 g |
| Diethylene Glycol | 3.5 g |
| Sodium Hydroxide | 4.0 g |
| Sodium Sulfite | 2.0 g |
| Sodium Acetate | 10.0 g |
| Citric Acid | 3.0 g |
| Tartaric Acid | 3.5 g |
| Potassium Bromide | 0.4 g |
| Sodium Chloride | 1.0 g |
| Ethylenediamine Tetraacetic Acid Di-sodium Salt | 4.0 g |
| Hydroxylamine Sulfate | 2.0 g |
| 4-Amino-3-methyl-N-ethyl-N-(β-methanesulfonamidoethyl)aniline Sesquisulfate Monohydrate | 5.0 g |
| Water to make | 1,000 ml |

Using the color developer thus prepared, 100 $m^2$ of a color paper was processed.

Thereafter, 1 l each of the developer thus used was treated in one of the following three processes (A), (B) and (C).

(A) The spent developer was brought into contact with 100 ml of XAD-7 (spherical methacrylate-glycol dimethacrylate copolymer, made by Rohm & Haas Co., having a mean diameter of about 1 mm, a specific surface area of 450 $m^2/g$ and a mean pore diameter of 90 A) using the same double walled tube and the same manner as in Example 4 and then the color developing agent was recovered using 1 N sulfuric acid.

(B) The same procedure as in (A) was followed using a column packed with 100 ml of activated carbon (Shirasagi, a trade name, made by Takeda Chemical Industries Co., Ltd., average particle size (diameter): 0.4 mm) in place of the XAD-7.

(C) The same procedure as in process (A) was followed using a column packed with 100 ml of a strongly basic anion exchange resin, Amberlite IRA-400 (trade name, produced by Rohm & Haas Co.), in place of the XAD-7.

The composition of the solution passed through the column was analyzed in each case. The results obtained are shown in Table 5 below.

TABLE 5

| | Before Passing Column (g/l) | After Passing Column (A) (g/l) | (B) (g/l) | (C) (g/l) |
|---|---|---|---|---|
| Benzyl Alcohol | 12.1 | 3.5 | 1.8 | 12.0 |
| Diethylene Glycol | 3.4 | 3.3 | 1.3 | 3.4 |
| Sodium Acetate | 9.8 | 9.6 | 1.1 | 1.0 |
| Ethylenediamine Tetraacetic Acid Di-sodium Salt | 3.9 | 3.9 | 1.8 | 0.5 |

TABLE 5-continued

| | Before Passing Column (g/l) | After Passing Column (A) (g/l) | (B) (g/l) | (C) (g/l) |
|---|---|---|---|---|
| Citric Acid | 2.9 | 2.8 | 0.5 | 0.3 |
| Tartaric Acid | 3.3 | 3.2 | 0.4 | 0.3 |
| 4-Amino-3-methyl-N-ethyl-N-(β-methanesulfonamidoethyl)-aniline Sesquisulfate Monohydrate | 4.9 | 0.9 | 0.6 | 4.5 |

As is clear from the above results, in process (A) wherein the color developer was brought into contact with the XAD-7, benzyl alcohol and the color developing agent, 4-amino-3-methyl-N-ethyl-N-(β-methanesulfonamidoethyl)aniline sesquisulfate monohydrate only were selectively removed from the developer.

On the other hand, in process (B) wherein the color developer was brought into contact with activated carbon, not only benzyl alcohol and the color developing agent but also diethylene glycol, sodium acetate, ethylenediamine tetraacetic acid di-sodium salt, citric acid, and tartaric acid were removed from the developer. That is, it was impossible to only remove selectively the benzyl alcohol and the color developing agent using the activated carbon.

Furthermore, in process (C) wherein the color developer was brought into contact with the ion exchange resin, the color developing agent and benzyl alcohol were hardly removed from the developer.

EXAMPLE 6

In this example, XAD-7 as the methacrylate copolymer used in Example 5 was regenerated and used repeatedly for the same purpose.

After passing water at 60° C. through the outer space of the double walled tube containing in the inside tube the methacrylate copolymer used in Example 5, 500 ml of 0.5 N sulfuric acid heated to 60° C. was passed through the column of the methacrylate copolymer over a period of 30 minutes. Thereafter, 4 l of city water was passed through the column of the copolymer over a period of 40 minutes to regenerate the methacrylate copolymer.

A spent color developer as in Example 5 was then brought into contact with the methacrylate copolymer thus regenerated and thereafter the copolymer was regenerated again using 0.5 N sulfuric acid. This procedure was repeated 20 times.

The compositions of the developer thus passed through the column of the copolymer at the 10th cycle and the 20th cycle are shown in Table 6 below.

TABLE 6

| | 10th Cycle (g/l) | 20th Cycle (g/l) |
|---|---|---|
| Benzyl Alcohol | 2.9 | 4.1 |
| Diethylene Glycol | 3.3 | 3.3 |
| Sodium Acetate | 9.8 | 9.8 |
| Ethylenediamine Tetraacetic Acid Di-sodium Salt | 3.9 | 3.9 |
| Citric Acid | 2.9 | 2.9 |
| Tartaric Acid | 3.2 | 3.2 |
| 4-Amino-3-methyl-N-ethyl-N-(β-methanesulfonamidoethyl)-aniline Sesquisulfate Monohydrate | 1.0 | 1.1 |

The results show that the compositions of the color developer at the 10th cycle and the 20th cycle were substantially the same as that of the developer at the 1st cycle, that is, the composition of the developer passed through the column of the copolymer in process (A) of Example 5. Thus, it was confirmed that the methacrylate copolymer used in the experiment could be regenerated by the very simple operation of bringing the copolymer used into contact with sulfuric acid and water and the copolymer thus regenerated could be used 20 times without substantially reducing the function by repeating the same regeneration cycle.

While the invention has been described in detail and with reference to specific embodiments thereof, it will be apparent to one skilled in the art that various changes and modifications can be made therein without departing from the spirit and scope thereof.

What is claimed is:

1. A process of selectively separating a p-phenylene diamine derivative from a photographic processing solution which comprises bringing the photographic processing composition into contact with a porous copolymer of a monoester of a monohydric alcohol or polyhydric alcohol and methacrylic acid and a polyester of a polyhydric alcohol and methacrylic acid, said copolymer being a porous copolymer having a pore volume of about 0.2 to about 1.5 ml/g, a specific area of about 100 to about 700 $m^2/g$ and a pore diameter of 30 to about 2,000 Å.

2. The process as set forth in claim 1, in which the photographic processing solution is a developer solution containing both of a developing agent and a color development accelerator.

3. The process as set forth in claim 1, in which the photographic processing solution is a color developer solution containing both a color developing agent and a color development accelerator.

4. The process as set forth in claim 1, in which the photographic processing solution is brought into contact with the copolymer by passing the processing solution through a column having the copolymer packed therein.

5. The process as set forth in claim 1, in which the photographic processing solution is brought into contact with the copolymer by placing the copolymer in the processing solution followed by stirring.

6. The process as set forth in claim 1, further including regenerating the copolymer brought into contact with the photographic processing solution by treating the copolymer with diluted sulfuric acid and water and repeatedly reusing the copolymer thus regenerated.

7. The process as set forth in claim 1, including recovering the p-phenylene diamine derivative thus adsorbed on the copolymer therefrom by treating the copolymer with diluted sulfuric acid.

8. The process of claim 1 wherein the photographic processing solution is a developer.

9. The process of claim 1 wherein the p-phenylene diamine derivative is removed by treating the copolymer with aqueous inorganic acid.

* * * * *